United States Patent
Nawamura et al.

(10) Patent No.: US 7,749,508 B2
(45) Date of Patent: Jul. 6, 2010

(54) **SKIN WHITENING METHOD USING *PLEUROTUS NEBRODENSIS***

(75) Inventors: Takeshi Nawamura, Yokohama (JP); Nobuhiko Ochiai, Yokohama (JP); Masato Hatao, Yokohama (JP); Mineyuki Yokoyama, Yokohama (JP); Koji Kobayashi, Yokohama (JP); Fumio Eguchi, Takasaki (JP)

(73) Assignees: Shiseido Co., Ltd., Chuo-ku, Tokyo (JP); Fumio Eguchi, Takasaki-shi, Gunma (JP)

( * ) Notice: Subject to any disclaimer, the term of this patent is extended or adjusted under 35 U.S.C. 154(b) by 0 days.

(21) Appl. No.: 12/365,985

(22) Filed: Feb. 5, 2009

(65) Prior Publication Data

US 2009/0226388 A1    Sep. 10, 2009

Related U.S. Application Data

(62) Division of application No. 10/571,206, filed on Oct. 27, 2006, now Pat. No. 7,510,716.

(51) Int. Cl.
*A61K 35/84* (2006.01)
(52) U.S. Cl. .................................... 424/195.15
(58) Field of Classification Search ............... None
See application file for complete search history.

(56) References Cited

U.S. PATENT DOCUMENTS

2003/0161842 A1 * 8/2003 Wang et al. ............. 424/195.15
2004/0137602 A1 * 7/2004 Kitajima et al. .......... 435/254.1

FOREIGN PATENT DOCUMENTS

| JP | 59-124984 | 7/1984 |
| JP | 5-317016 | 12/1993 |
| JP | 6-65575 | 3/1994 |
| JP | 6-219933 | 8/1994 |
| JP | 7-316026 | 12/1995 |
| JP | 7-316035 | 12/1995 |
| JP | 2002-348247 | 12/2002 |
| JP | 2004-107284 | 4/2004 |
| JP | 2006-241115 | 9/2006 |
| JP | 2007-70306 | 3/2007 |

OTHER PUBLICATIONS

Japanese Patent Abstract Publication No. 05-317016 published Dec. 3, 1993, eight pages.
Japanese Patent Abstract Publication No. 06-219933 published Aug. 9, 1994, 11 pages.
Japanese Patent Abstract Publication No. 06-065575 published Mar. 8, 1994, six pages.
Japanese Patent Abstract Publication No. 07-316026 published Dec. 2, 1995, 13 pages.
Japanese Patent Abstract Publication No. 59-124984 published Jul. 19, 1984, one page.
Japanese Patent Abstract Publication No. 2002-348247 published Dec. 4, 2002, eight pages.
Japanese Patent Abstract Publication No. 2004-107284 published Apr. 8, 2004, 11 pages.
Japanese Patent Abstract Publication No. 2006-241115 published Sep. 14, 2006, 14 pages.
Japanese Patent Abstract Publication No. 2007-070306 published Mar. 22, 2007, 13 pages.
Japanese Patent Abstract Publication No. 07-316035 published Dec. 5, 1995, 21 pages.
International Search Report for PCT/JP2004/013198 mailed Dec. 28, 2004, two pages.

* cited by examiner

*Primary Examiner*—Christopher R. Tate
(74) *Attorney, Agent, or Firm*—Rankin, Hill & Clark LLP

(57) ABSTRACT

The present invention provides an antioxidant and a whitening agent having high safety, and a external preparation for skin using the same. The antioxidant and whitening agent comprise, as an effective component, one or more extracts from *Basidiomycetes* selected from the group consisting of *Pleurotus abalonus, Pholiota squarrosa, Onnia orientalis, Astraeus hygrometricus* and *Pleurotus nebrodensis*. These extracts have a free radical capturing ability and are useful for suppressing skin oxidation and for preventing and improving skin aging. In addition, the extracts have a tyrosinase activity inhibiting action and can suppress the melanin generation. Since the fruit bodies of these *Basidiomycetes* have been used for edible purpose and have high safety, they can be used preferably for an external preparation for skin.

10 Claims, 7 Drawing Sheets

SKIN WHITENING METHOD USING *PLEUROTUS NEBRODENSIS*

RELATED APPLICATIONS

This application is a divisional application of U.S. patent application Ser. No. 10/571,206 filed Oct. 27, 2006, now U.S. Pat. No. 7,510,716 which claims the priority of Japanese Patent Application No. 2003-318578 filed on Sep. 10, 2003, Japanese Patent Application No. 2004-148880 filed on May 19, 2004, and Japanese Patent Application No. 2004-236612 filed on Aug. 16, 2004, which are incorporated herein by reference.

FIELD OF THE INVENTION

The present invention relates to an antioxidant, a whitening agent and an external preparation for skin using the same, in particular to an effective component thereof. In particular, the invention relates to suppression of melanin generation, inhibition of tyrosinase activity and skin-whitening using the extract of *Pleurotus nebrodensis*.

BACKGROUND OF THE INVENTION

It is well known that ultraviolet rays generate active oxygen. When free radical type active oxygen among this active oxygen reacts with lipids or the like, a chain oxidation reaction is induced. Accordingly, free radicals cause enhanced damages to tissues.

Since skin is always exposed to oxygen and ultraviolet rays, it is one of the organs which are damaged by such stress from oxidization. In recent years, it has been considered that various types of active oxygen generated by ultraviolet rays causes peroxidation of sebum and lipids, denaturation of proteins, inhibition of enzymes and the like, thereby inducing inflammation of skin over the short term, and in addition, leading to aging, cancer and the like over the long term. Furthermore, it is believed that active oxygen and lipid peroxide are related to skin diseases such as atopic dermatitis, contact dermatitis and psoriasis. In this manner, active oxygen (free radicals) is deeply associated with skin aging and skin diseases.

Substances having an ability to capture free radicals can suppress and/or stop radical chain reaction. Accordingly, external preparations for skin using such antioxidants can be expected to be effective in preventing and/or improving skin aging (for example, spots, wrinkles and sagging) caused by stress from photo oxidation. In addition, they can also be expected to have preventive and/or improvement effects as external preparations for various skin diseases associated with free radicals.

Vitamins E and C are free radical capturing-type antioxidants in organisms. In addition, synthetic antioxidants, such as BHT and BHA, are also known.

However, the antioxidant ability (free radical capturing ability) of these substances cannot be said to be sufficient, and it is suspected that BHT and BHA are carcinogenic.

Accordingly, an antioxidant which has an excellent free radical capturing ability as well as high safety for skin has been desired.

Meanwhile, skin pigmentation, such as spots and freckles, is caused by excessive pigmentation of melanin due to hormonal abnormality or ultraviolet stimulation as a trigger, which enhances the melanin generation within pigment cells in epidermis.

For preventing such spots and freckles, a method by administrating or applying a substance which can suppress the melanin generation have conventionally been used. Specifically, it includes, for example, a method by administrating a large amount of L-ascorbic acid, a method by injecting glutathione or the like, and a method by locally applying kojic acid, cysteine, hydroquinone or the like, in such forms as ointments, creams, lotions.

At present, however, no substance satisfactory in effects, stability, safety and the like has been obtained.

As for natural anti-oxidants, extracts from Shiitake (*Lentinus edodes*), Enokitake (*Flammulina velutipes*), Shimeji (*Lyophyllum decastes*), Kawaratake (*Coriolus versicolor*), Matsutake (*Tricholoma matsutake*), Mannentake (*Ganoderma lucidum*), Hourokutake (*Daedalea dickinsii*), Nameko (*Pholiota nameko*) and other *Basidiomycetes* have been reported (Japanese Unexamined Patent Publication Nos. 5-317016, 6-65575, and 59-124984).

However, for extracts from *Onnia orientalis*, *Astraeus hygrometricus* or *Pleurotus nebrodensis*, no free radical capturing ability, antioxidative ability, melanin generation suppressive effect or application to external preparations for skin thereof has been known.

In addition, for extracts from *Pleurotus abalones*, although the platelet aggregation inhibition effect and rough skin improvement effect have been reported (Japanese Unexamined Patent Publication No. 2002-348247), no radical capturing ability, antioxidative ability or melanin generation suppressive effect thereof has been known.

Furthermore, for *Pholiota squarrosa*, although the production of a substance capable of degrading melanin by culturing mycelium thereof has been reported (Japanese Unexamined Patent Publication No. 2004-107284), no radical capturing ability, antioxidative ability or melanin generation suppressive effect thereof has been known.

DISCLOSURE OF THE INVENTION

Problem to be Solved by the Invention

The present invention has been made in view of the above-described problems with the prior art and the object is to provide an antioxidant which has an excellent free radical capturing ability and high safety, and to provide as an external preparation for skin using the same. Also, it is to provide a whitening agent which has an excellent melanin generation suppressive effect and high safety, and to provide an external preparation for skin using the same.

Means to Solve the Problem

In order to achieve the above-described objects, the present inventors conducted diligent studies, and as a result, found that an extract from specific *Basidiomycetes* have a free radical capturing ability and are useful as an antioxidant. In addition, it became clear that these also have a melanin generation suppressive effect, and thus, the present invention was completed.

That is to say, an antioxidant according to the present invention comprises, as an effective component, one or more extracts from *Basidiomycetes* selected from the group consisting of *Pleurotus abalonus*, *Pholiota squarrosa*, *Onnia orientalis*, *Astraeus hygrometricus* and *Pleurotus nebrodensis*.

An antioxidative external preparation for skin according to the present invention comprises one or more extracts from *Basidiomycetes* selected from the group consisting of *Pleurotus abalonus, Pholiota squarrosa, Onnia orientalis, Astraeus hygrometricus and Pleurotus nebrodensis.

An external preparation for skin according to the present invention comprises one or more extracts from Basidiomycetes selected from the group consisting of Onnia orientalis, Astraeus hygrometricus and Pleurotus nebrodensis.

A whitening agent according to the present invention comprises, as an effective component, one or more extracts from Basidiomycetes selected from the group consisting of Pleurotus abalonus, Pholiota squarrosa, Onnia orientalis, Astraeus hygrometricus and Pleurotus nebrodensis.

A melanin generation suppressing agent according to the present invention comprises, as an effective component, one or more extracts from Basidiomycetes selected from the group consisting of Pleurotus abalonus, Pholiota squarrosa, Onnia orientalis, Astraeus hygrometricus and Pleurotus nebrodensis.

EFFECTS OF THE INVENTION

The extract from Pleurotus abalonus, Pholiota squarrosa, Onnia orientalis, Astraetis hygrometricus or Pleurotus nebrodensis has a free radical capturing ability and an antioxidative effect. The fruit bodies (mushrooms) of these Basidiomycetes have been known to be used for medical or edible purposes, and are highly safe. Accordingly, the antioxidant of the present invention can be used in a variety of fields, and preferably, in fields of cosmetics, pharmaceuticals, quasi-drugs, foods and the like in particular.

In addition, external preparations for skin using the antioxidant of the present invention can suppress skin oxidation by capturing free radicals in skin, and are useful for preventing and improving skin aging, such as spots, wrinkles and sagging. Further, effects in preventing and improving dermatosis, which is associated with free radicals, can also be expected.

Furthermore, since extracts from Pleurotus abalonus, Pholiota squarrosa, Onnia orientalis, Astraeus hygrometricus and Pleurotus nebrodensis can inhibit the activity of tyrosinase and suppress the melanin generation, they are useful as whitening agents.

BEST MODE FOR CARRYING OUT THE INVENTION

Figure 1:
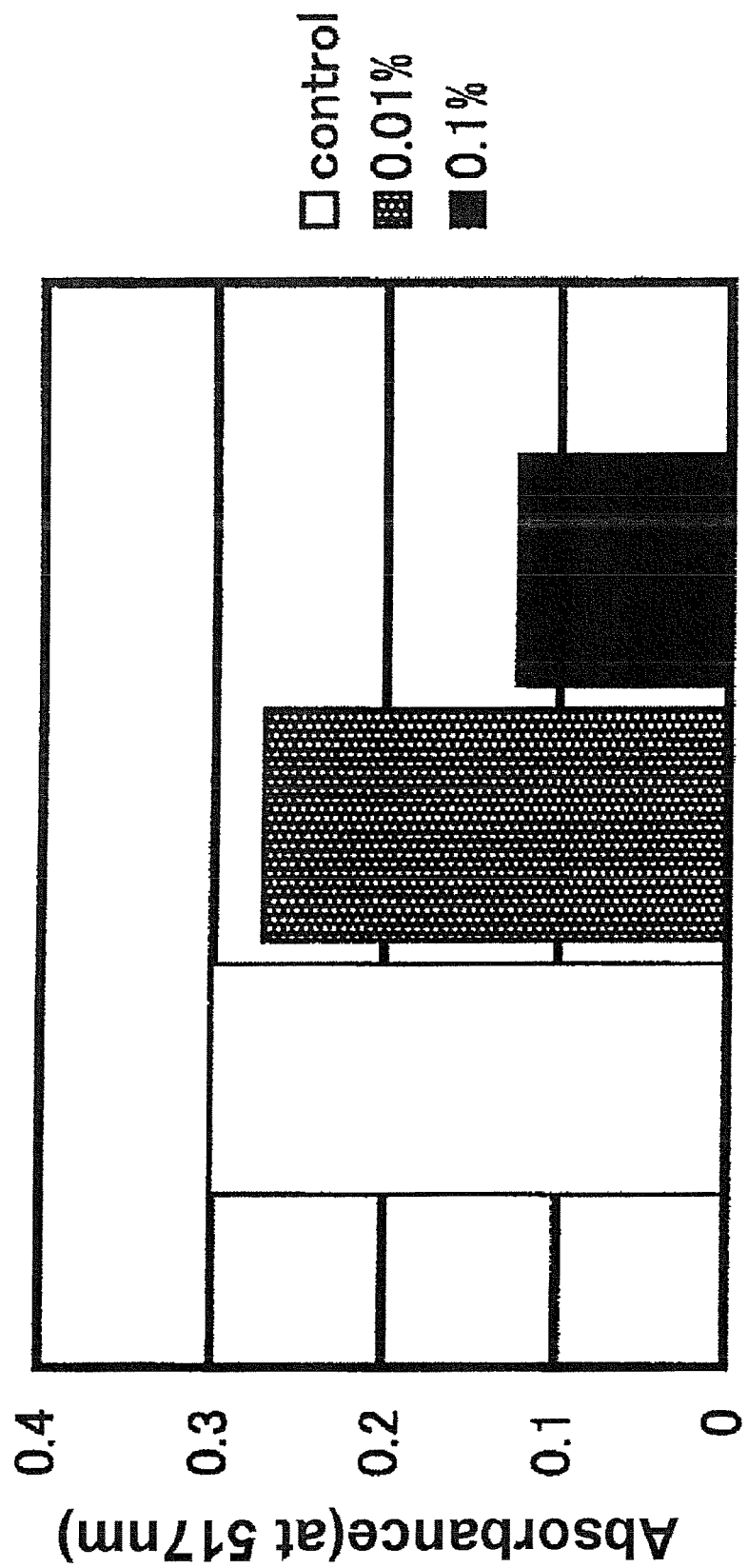
FIG. 1 is a graph that shows a free radical capturing activity of the extract from Pleurotus abalones fruit body in accordance with an example of the invention.

The Japanese names and classifications for Pleurotus abalonus, Pholiota squarrosa, Onnia orientalis, Astraeus hygrometricus and Pleurotus nebrodensis, which are Basidiomycetes used in the present invention, are as follows.

Pleurotus abalonus (Kuroawabitake): Pleurotaceae Pleurotus

Pholiota squarrosa (Sugitake): Strophiaceae Pholiota

Onnia orientalis (Azumatake): Hymenochaetaceae Onnia

Astraeus hygrometricus (Tsutiguri): Astraeaceae Astraeus

Pleurotus nebrodensis is a basidiomycete which belongs to Pleurotaceae Pleurotus, and no formal Japanese name has yet been given. However, the mushroom thereof is commercially available under a number of trade names, for example, "Yukireitake" (by Agricultural Union Corporation Neoplants, Akagi Kinoko Hompo (LLC), or Karasawa Sangyo (LLC)).

Here, the scientific characteristics and other information of Pleurotus nebrodensis are as follows.

1. Scientific Characteristics

Characteristics of fungus: white colonies are formed in nutrient culture medium containing a carbon source and a nitrogen source. In addition, clamp connections are observed through an optical microscope.

2. Taxonomic Position

Basidiomycete

3. Culture Condition (1) Name of Culture Medium

SMYA culture medium (S: saccharose, M: malto extract, Y: yeast extract, A: agar)

S and A: commercially available M and Y: made by Difco Corporation (2) Culture Medium Composition (per 1000 ml of culture medium)

| | |
|---|---|
| 1% saccharose | (10 g) |
| 1% malto extract | (10 g) |
| 0.4% yeast extract | (4 g) |
| 2% agar | (20 g) |

(3) pH of Culture Medium: 5.0-7.0 (optimal pH is 5.5)

(4) Condition for Sterilizing Culture Medium: at 121° C., for 20 minutes (5) Temperature of Culture Medium: at 28° C.

(6) Culture Period: for 10 days (7) Oxygen Requiring Property: aerobic

4. Storage Condition

A Freezing method can be used for storage.

(1) Freezing Condition: at −80° C.

(2) Protective Agent: 10-20% glycerin aqueous solution (20% is optimal)

(3) Restoration Ratio after Freezing: 100% after one year, 99% after three years 5. Conditions for Survival Test (1) Restoration of Microorganisms: at 40° C.

(2) Methods for Inoculation, Culture and Confirmation: same as the Culture Condition Any fruit bodies (mushrooms) of Basidiomycetes according to the present invention grow naturally or are cultivated in Japan, and they are provided for a medicinal or edible purpose. However, it has not been reported so far that extracts from these mushrooms have a free radical capturing ability, an antioxidative ability or a melanin generation suppressive effect, and the present inventors have clarified these for the first time.

In the present invention, it is preferable to use fruit bodies (mushrooms) for the extraction. The fruit bodies may be raw or dried, and from the point of view of handling, preservation and extraction efficiency, dried fruit bodies are desirable. In addition, the effects can be expected for mycelium. Although raw or dried mycelium that is obtained by culturing inoculums in medium containing a carbon source and a nitrogen source can be used, dried mycelium are convenient to be used.

In the present invention, any *Basidiomycetes* which grow naturally or are cultivated can be used, and in addition, a mixture of two or more extracts from *Basidiomycetes* mentioned above may be used.

Prior to providing extracts, it is preferable to destroy the tissue, and thereby carrying out the extraction efficiently. As for the means for destroying the tissue, there include grinding processes using a variety types of grinding mixers, such as bead mills, whirling blenders and homogenizers; impact crushing processes using blasting machines or the like; freezing processes; physical processes, such as ultrasonication; alkaline processes using an aqueous solution such as that of sodium hydroxide; processes using enzymes having a cell wall degradation effect, such as cellulase and pectinase; and chemical processes, such as osmotic pressure processes, which can be carried out alone or in combinations appropriately.

In the enzyme processes, well-known cell wall degrading enzymes or polysaccharide degrading enzymes can be used, and one or more enzymes selected from cellulase, hemicellulase, chitinase, $\alpha$- and $\beta$-glucuronidase, pectinase, xylanase, $\alpha$- and $\beta$-glucanase and the like can be used. In the enzyme process, an aqueous solution of the above-described enzymes may be added to mushrooms which have been cut finely or grinded appropriately, and then shaken or stirred.

As for the method for producing extracts of the present invention, the mushrooms tissue which has been destroyed as described above, with a extracting solvent added thereto, may be appropriately stirred, and then extracted. As a solvent for extraction, there are no particular limitations as long as the effects of the present invention are not deteriorated. For example, water; primary alcohols, such as methanol and ethanol; polyvalent alcohols, such as 1,3-butylene glycol and propylene glycol; lower alkyl esters, such as ethyl acetate; aromatic carbons, such as benzene and hexane; ethyl ether; acetone; and the like can be used. In the present invention, two or more solvents thereof may be combined for use. Preferable solvents include water, methanol, ethanol, 1,3-butylene glycol or a mixture thereof. Here, the residue of extraction may be extracted again under the same conditions as those described above, and this extraction operation may be repeated several times. The liquid extract can be used as an extract, or the resulting obtained by removing the solvent of the liquid extract out in accordance with an appropriate known method, such as condensation under reduced pressure, can be used as a extract.

In the external preparation for skin of the present invention, the extract from *Pleurotus abalonus, Pholiota squarrosa, Onnia orientalis, Astraeus hygrometricus* or *Pleurotus nebrodensis* is, as dry weight, 0.001-20.0 wt %, preferably 0.01-10.0 wt % with respect to the entire composition. In the case of less than 0.001 wt %, the effects of the present invention cannot sufficiently be obtained, while in the case where it exceeds 20.0 wt %, a further and substantial increase in the effects cannot be expected, and mixing into an external preparation for skin tends to become difficult. Here, *Pleurotus nebrodensis* extract is particularly preferable for a whitening agent.

In addition to the above described essential components, components which are conventionally used for external preparations for skin in cosmetics or pharmaceuticals, for example, whitening agents, moisturizing agents, antioxidants, oils, ultraviolet absorbents, surfactants, thickeners, alcohols, powders, coloring materials, water soluble materials, water, various nutrients for skin, various medicaments, chelating agents, pH adjusting agents and the like, can be added appropriately into the external preparations for skin of the present invention, if necessary.

The term "external preparation for skin" in the present invention refers to products which are conventionally used in the field of pharmaceuticals, quasi-drugs, cosmetics and the like. The product form is not particularly limited as long as the effects of the present invention can be obtained. Any form conventionally used for external preparations for skin, including ointments, creams, milky lotions, lotions, packs and bath preparations may be used.

In the following, the present invention is further described in detail by Examples, but not limited thereto. Here, a compounding amount is wt % unless otherwise specified.

EXAMPLE 1

Antioxidative Activity Test for Mushroom Extracts (1) Preparation of Liquid Extracts from Mushrooms 80 ml of methanol was added to 10 g of dried powder of fruit bodies and left for 7 days at room temperature to provide a liquid extract with methanol. Next, the methanol extract was filtered through a filter paper and condensed by an evaporator. Then, the residue was dried under reduced pressure to give a mushroom extract. The extract from each mushroom was dissolved in an appropriate amount of methanol (ethanol for *Onnia orientalis* and DMSO for *Pleurotus nebrodensis*) to be used as a test solution in the following experiments. Here, strains which were used in these experiments were as follows.

*Pleurotus abalonus*: FCE732

*Pholiota squarrosa*: FCE1561

*Onnia orientalis*: FCE660, FCE659, FCE661

*Astraeus hygrometricus*: FCE2500

*Pleurotus nebrodensis*: No. 17

(2) Measurement of Antioxidative Activity (Free Radical Capturing Activity)

The measurement of the antioxidative activity was carried out using a DPPH method. DPPH (1,1-diphenyl-2-picrylhydrazyl) that had been dissolved in ethanol in advance was added to each test solution so that the final concentration became 0.1 mM, and the mixture was stirred. After being left for 10 minutes at room temperature, the absorbance was measured at 517 nm. The value measured for the solvent (methanol, ethanol or DMSO) only, which did not contain any extracts, was used as a control.

(3) Results

Figure 2:
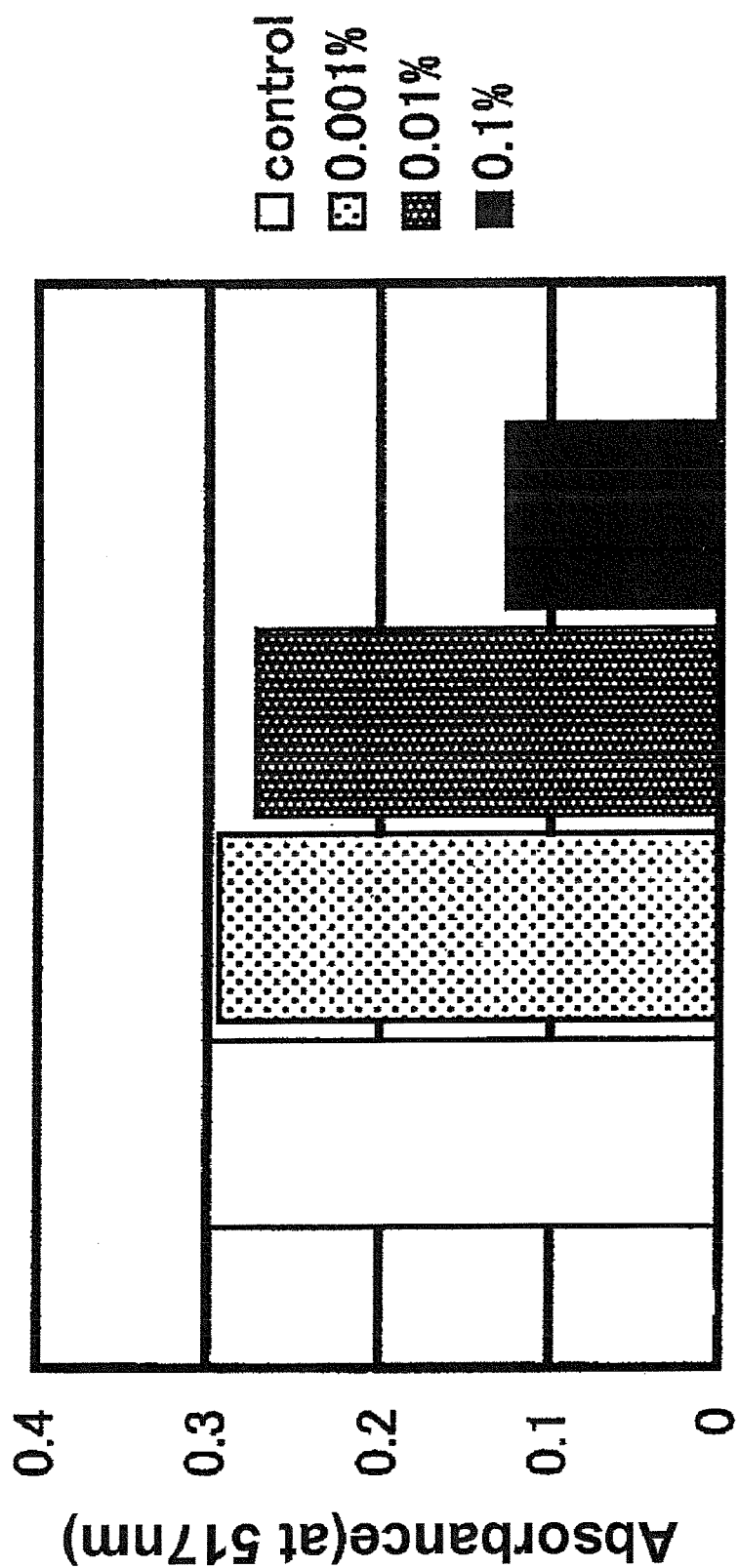
FIG. 2 is a graph that shows a free radical capturing activity of the extract from Pholiota squarrosa fruit body in accordance with an example of the invention.
Figure 3:
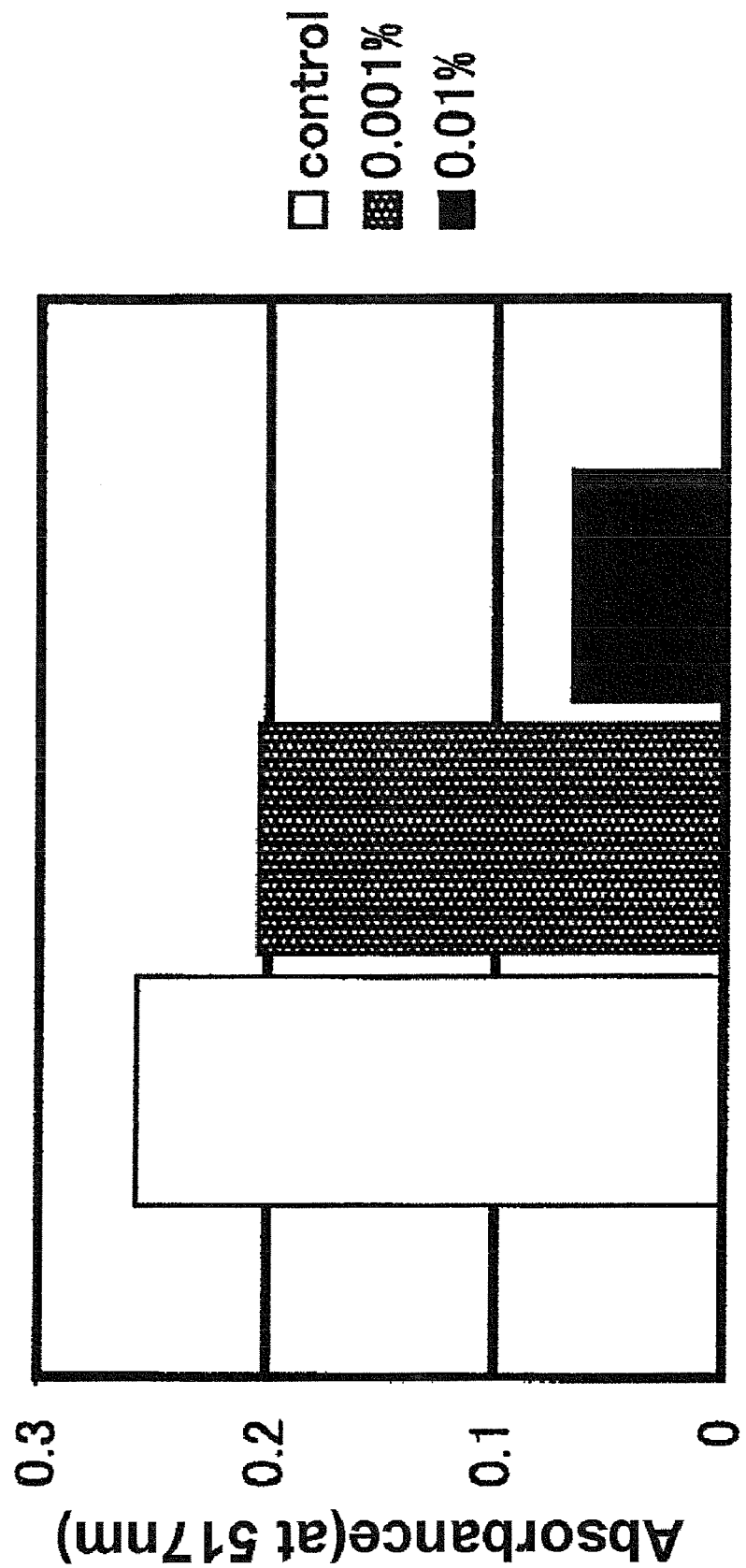
FIG. 3 is a graph that shows a free radical capturing activity of the extract from Onnia orientalis fruit body in accordance with an example of the invention.
Figure 4:
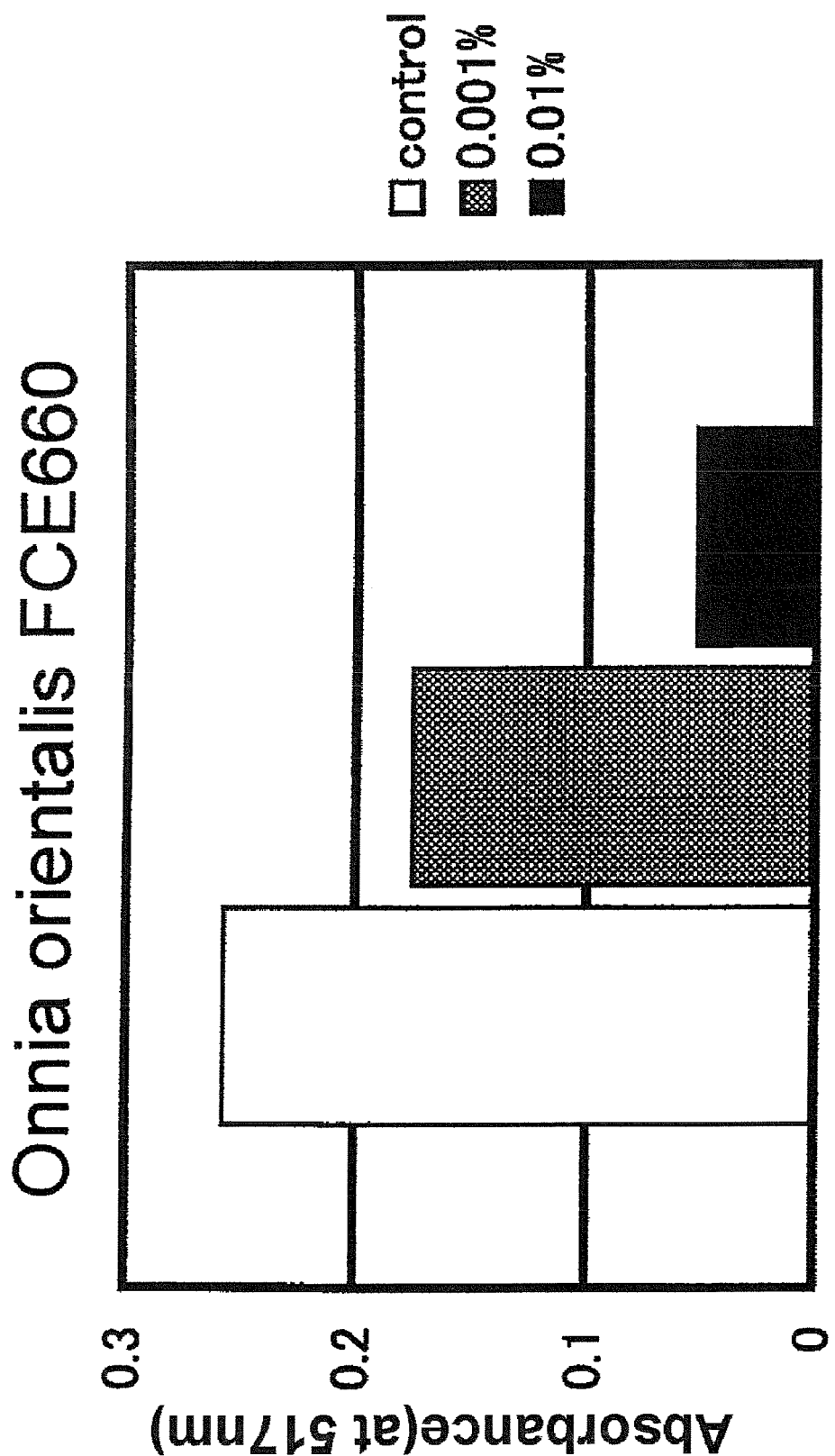
FIG. 4 is a graph that shows a free radical capturing activity of the extract from Onnia orientalis fruit body in accordance with an example of the invention.
Figure 5:
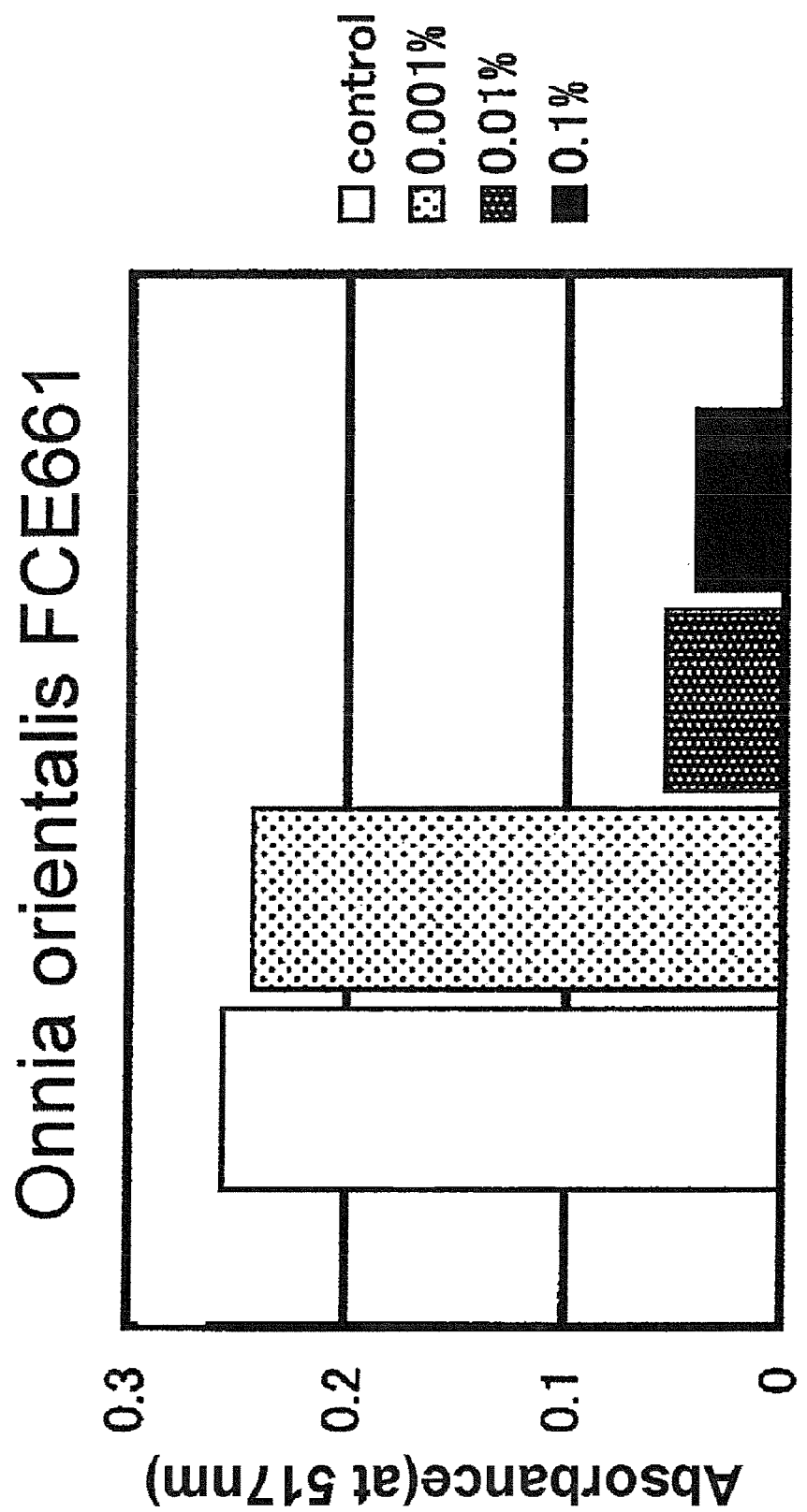
FIG. 5 is a graph that shows a free radical capturing activity of the extract from Onnia orientalis fruit body in accordance with an example of the invention.
Figure 6:
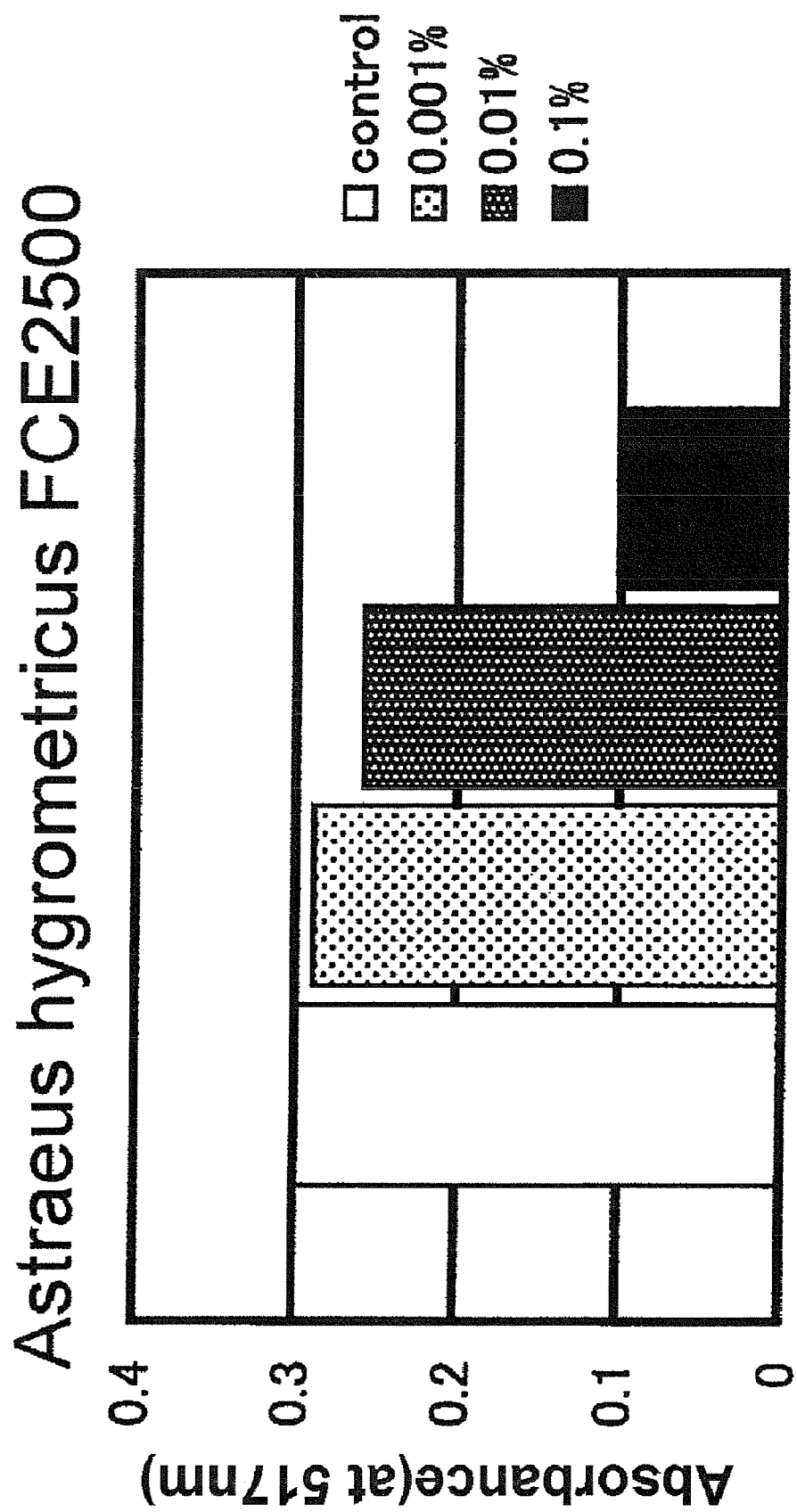
FIG. 6 is a graph that shows a free radical capturing activity of the extract from Astraeus hygrometricus fruit body in accordance with an example of the invention.
Figure 7:
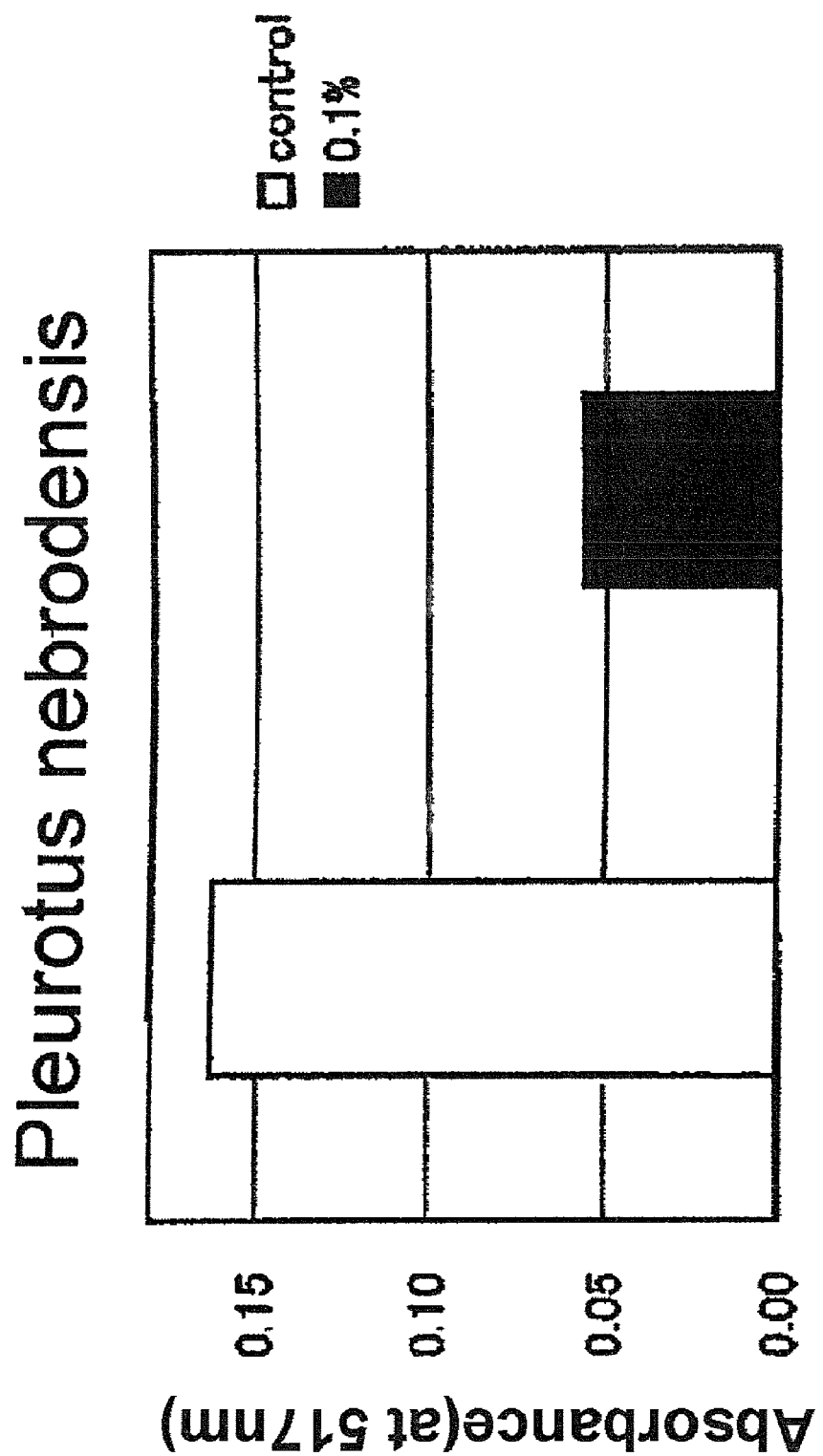
FIG. 7 is a graph that shows a free radical capturing activity of the extract from Pleurotus nebrodensis fruit body in accordance with an example of the invention.

As can be seen from FIGS. 1 to 7, a free radical capturing activity was demonstrated in any extracts from fruit bodies of *Pleurotus abalonus, Pholiota squarrosa, Onnia orientalis, Astraeus hygrometricus* and *Pleurotus nebrodensis*. Accordingly, it can be understood that the extracts thereof can be used as a free radical capturing type antioxidant.

EXAMPLE 2

Tyrosinase Activity Inhibiting Test for Mushroom Extracts (1) Preparation of Liquid Extracts from Mushrooms A test solution was prepared in the same manner as the above-described Example 1(1), and was used as a sample solution.

(2) Cell Culturing Method

B16 melanoma culture cells derived from mice were used. The cells were cultured in an Eagle's MEM medium, which contains 10% FBS and/or theophylline (0.09 mg/ml), within a $CO_2$ incubator (95% air, 5% carbon dioxide) at 37° C. After 24 hours of culturing, the sample solution was added thereto so that the final concentration (as dried extract concentration) became 0.01-0.1 wt %. After culturing was continued for an additional three days, the produced amount of melanin was determined visually and the tyrosinase activity inhibitory effect was measured in accordance with the following methods.

(3) Visual Determination of Melanin Amount

A diffusion plate was placed on the lid of a well plate, and the amount of melanin within the cells was observed through an inverted microscope and compared with a reference sample to which no mushroom extracts were added. The score and criteria were as follows.

<Score: Criteria>

−2: whiter in comparison with the reference, and determined that the amount of melanin was small.

−1: slightly whiter in comparison with the reference, and determined that the amount of melanin was slightly small.

0: equally white in comparison with the reference, and determined that the amount of melanin was approximately the same.

(4) Measurement of Tyrosinase Activity

The medium in the well was removed before the measurement, and the well was washed twice with 100 µl of PBS. 45 µl of PBS supplemented with 1% triton-X (made by Rohm and Haas Company, surfactant), was added to each well. The plate was shaken for 1 minute to destroy the cell walls well, and then the absorbance was measured at 475 nm by a microplate reader to provide the absorbance at 0 minute. Then, 5 µl of 10 mM L-DOPA solution was immediately added thereto, and the plate was transferred into an incubator at 37° C. and reacted for 60 minutes. After the plate was shaken for 1 minute, the absorbance (at 475 nm) was measured to provide the absorbance at 60 minutes. The difference in absorbance between at 0 minute and 60 minutes was calculated and the ratio of the difference in the sample containing the mushroom extract with respect to that of control without the mushroom extract was obtained as the tyrosinase activity ratio (%).

(5) Results

TABLE 1

| | Concentration of *Pleurotus nebrodensis* (%) | | |
|---|---|---|---|
| | 0.01 | 0.03 | 0.1 |
| Evaluation of Visual Determination | −1 | −2 | −2 |
| Tyrosinase Activity Ratio (%) | 96 | 94 | 43 |

As shown in Table 1, the extracts from mushrooms of the present invention have an excellent melanin generation suppressive effect and a tyrosinase activity inhibitory effect, and thus are useful as a whitening agent.

EXAMPLE 3

Formulation Examples of external preparations for skin according to the present invention are shown in the following.

Formulation Example 1 Lotion

| | |
|---|---|
| Ethyl alcohol | 5 |
| Glycerin | 1 |
| 1,3-Butylene glycol | 5 |
| Polyoxyethylene polyoxypropylene decyltetradecyl ether | 0.2 |
| Sodium hexametaphosphate | 0.003 |
| Trimethylglycine | 1 |
| Sodium polyaspartate | 0.1 |
| Potassium 2-L-ascorbyl α-tocopherol phosphate | 0.1 |
| Thiotaurine | 0.1 |
| Green tea extract | 0.1 |
| Peppermint extract | 0.1 |
| Orris extract | 0.1 |
| *Astraeus hygrometricus* extract with ethanol | 0.1 |
| Trisodium HEDTA | 0.1 |
| Carboxyvinyl polymer | 0.05 |
| Potassium hydroxide | 0.02 |
| Phenoxy ethanol | Q.S. |
| Purified water | Balance |
| Perfume | Q.S. |

Formulation Example 2

Lotion

| | |
|---|---|
| Glycerin | 2 |
| 1,3-Butylene glycol | 4 |
| Erythritol | 1 |
| Polyoxyethylene methyl glucoside | 1 |
| Polyoxyethylene hardened castor oil | 0.5 |
| *Onnia orientalis* liquid extract with 50% 1,3-butylene glycol (residual content when dried: 1%) | 0.1 |
| Citric acid | 0.02 |
| Sodium citrate | 0.08 |
| Phenoxy ethanol | Q.S. |
| Ethyl L-cocoyl arginine DL-pyrolidonecarboxylic acid | 0.1 |
| Purified water | Balance |

Formulation Example 3

Milky Lotion

| | |
|---|---|
| Dimethylpolysiloxane | 3 |
| Decamethylcyclopentasiloxane | 4 |
| Ethanol | 5 |
| Glycerin | 6 |
| 1,3-Butylene glycol | 5 |
| Polyoxyethylene methyl glucoside | 3 |
| Sunflower oil | 1 |
| Squalane | 2 |
| Potassium hydroxide | 0.1 |
| Sodium hexametaphosphate | 0.05 |
| Hydroxypropyl-β-cyclodextrin | 0.1 |
| Dipotassium glycyrrhizinate | 0.05 |
| Loquat extract | 0.1 |

-continued

| | |
|---|---|
| Sodium L-glutamate | 0.05 |
| Fennel extract | 0.1 |
| Yeast extract | 0.1 |
| Lavender oil | 0.1 |
| *Rehmannia* extracts | 0.1 |
| *Pholiota squarrosa* extract with 50% ethanol | 0.1 |
| Dimorphorinopyridazinone | 0.1 |
| Xanthan gum | 0.1 |
| Carboxyvinyl polymer | 0.1 |
| Acrylic acid/alkyl methacrylate copolymer (Pemulen TR-1) | 0.1 |
| Red iron oxide | Q.S. |
| Yellow iron oxide | Q.S. |
| Paraben | Q.S. |
| Purified water | Balance |

Formulation Example 4

Milky Lotion

| | |
|---|---|
| Dimethylpolysiloxane | 2 |
| Decamethylcyclopentasiloxane | 25 |
| Dodecamethylcyclohexasiloxane | 10 |
| Polyoxyethylene/methylpolysiloxane copolymer | 1.5 |
| Trimethylsiloxysilicate | 1 |
| 1,3-Butylene glycol | 5 |
| Squalane | 0.5 |
| Talc | 5 |
| Dipotassium glycyrrhizinate | 0.1 |
| *Pleurotus abalonus* extract with ethanol | 0.1 |
| Tocopherol acetate | 0.1 |
| Trisodium edetate | 0.05 |
| 4-t-Butyl-4'-methoxydibenzoylmethane | 1 |
| 2-Ethylhexyl p-methoxycinnamate | 5 |
| Glyceryl mono-2-ethylhexanoate di-p-methoxycinnamate | 1 |
| Silicone coated titanium oxide fine particle (40 nm) | 4 |
| Dimethy ldistearyl ammonium hectolite | 0.5 |
| Spherical polyethylene powder | 3 |
| Phenoxy ethanol | Q.S. |
| Purified water | Balance |
| Perfume | Q.S. |

Formulation Example 5

Milky Lotion

| | |
|---|---|
| Liquid paraffin | 7 |
| Vaseline | 3 |
| Decamethylcyclopentasiloxane | 2 |
| Behenyl alcohol | 1 |
| Glycerin | 5 |
| Dipropylene glycol | 7 |
| Polyethylene glycol 1500 | 2 |
| Jojoba oil | 1 |
| Isostearic acid | 0.5 |
| Stearic acid | 0.5 |
| Behenic acid | 0.5 |
| Pentaerythritol tetra-2-ethylhexanoate | 3 |
| Cetyl 2-ethylhexanoate | 3 |
| Glyceryl monostearate | 1 |
| Polyoxyethylene glyceryl monostearate | 1 |
| Potassium hydroxide | 0.1 |
| Sodium hexametaphosphate | 0.05 |
| Stearyl glycyrrhizinate | 0.05 |
| L-Arginine | 0.1 |
| Royal jelly extract | 0.1 |
| Yeast extract | 0.1 |

-continued

| | |
|---|---|
| *Pholiota squarrosa* extract with ethyl acetate | 0.01 |
| Tocopherol acetate | 0.1 |
| Acetylated hyaluronic acid sodium salt | 0.1 |
| Trisodium edetate | 0.05 |
| 4-t-butyl-4'-methoxydibenzoylmethane | 0.1 |
| 2-ethylhexyl p-methoxycinnamate | 0.1 |
| carboxyvinyl polymer | 0.15 |
| paraben | Q.S. |
| purified water | Balance |
| perfume | Q.S. |

Formulation Example 6

Cream

| | |
|---|---|
| α-Olefin oligomer | 10 |
| Vaseline | 1 |
| Microcrystalline wax | 3 |
| Decamethylcyclopentasiloxane | 5 |
| Glycerin | 10 |
| Dipropylene glycol | 2 |
| 1,3-Butylene glycol | 2 |
| Erythritol | 2 |
| Squalane | 1 |
| Glycerin fatty acid ester eicosanic acid condensate | 0.1 |
| Isostearic acid | 1 |
| Cetyl 2-ethylhexanoate | 5 |
| Sodium chloride | 0.5 |
| Sodium hexametaphosphate | 0.05 |
| Stearyl glycyrrhizinate | 0.05 |
| Yeast extract | 0.1 |
| Magnesium L-ascorbylphosphate | 2 |
| Tocopherol acetate | 0.5 |
| Thiotaurine | 0.1 |
| Sodium DL-pyrrolidonecarboxylate | 1 |
| *Curcuma* extract | 0.1 |
| *Astraeus hygrometricus* extract with 50% ethanol | 0.1 |
| Trisodium edetate | 0.1 |
| Dimethyl ldistearyl ammonium hectolite | 2 |
| Sodium carboxylmethyl cellulose | 0.1 |
| Paraben | Q.S. |
| Purified water | Balance |
| Perfume | Q.S. |

Formulation Example 7

Cream

| | |
|---|---|
| Liquid paraffin | 8 |
| Vaseline | 3 |
| Dimethylpolysiloxane | 2 |
| Stearyl alcohol | 3 |
| Behenyl alcohol | 2 |
| Glycerin | 5 |
| Dipropylene glycol | 4 |
| Trehalose | 1 |
| Pentaerythritol tetra-2-ethylhexanoate | 4 |
| Polyoxyethylene glyceryl monoisostearate | 2 |
| Polyoxyethylene glyceryl monostearate | 1 |
| Lipophilic glyceryl monostearate | 2 |
| Citric acid | 0.05 |
| Sodium citrate | 0.05 |
| Potassium hydroxide | 0.015 |
| Oil soluble licorice extract | 0.1 |
| Retinol palmitate (1,000,000 units) | 0.25 |
| Tocopherol acetate | 0.1 |

-continued

| | |
|---|---|
| *Pleurotus abalonus* extract with 50% ethanol | 0.1 |
| Paraoxybenzoate | Q.S. |
| Phenoxy ethanol | Q.S. |
| Dibutylhydroxytoluene | Q.S. |
| Trisodium edetate | 0.05 |
| 4-t-Butyl-4'-methoxydibenzoylmethane | 0.01 |
| 2-Ethylhexyl p-methoxycinnamate | 0.1 |
| β-Carotene | 0.01 |
| Polyvinyl alcohol | 0.5 |
| Hydroxyethyl cellulose | 0.5 |
| Carboxyvinyl polymer | 0.05 |
| Purified water | Balance |
| Perfume | Q.S. |

Formulation Example 8

Two Layer Type Cream

| | |
|---|---|
| Dimethylpolysiloxane | 5 |
| Decamethylcyclopentasiloxane | 25 |
| Trimethylsiloxysilicate | 5 |
| Polyoxyethylene/methylpolysiloxane copolymer | 2 |
| Dipropylene glycol | 5 |
| Dextrin palmitate coated zinc oxide fine particle (60 nm) | 15 |
| Dipotassium glycyrrhizinate | 0.02 |
| Glutathione | 1 |
| Thiotaurine | 0.05 |
| *Sophora Angustifolia* extract | 1 |
| *Onnia orientalis* liquid extract with 1,3-butylene glycol (residual content when dried: 0.1%) | 5 |
| Paraben | Q.S. |
| Phenoxy ethanol | Q.S. |
| Trisodium edetate | Q.S. |
| 2-Ethylhexyl p-methoxycinnamate | 7.5 |
| Dimethyl distearyl ammonium hectolite | 0.5 |
| Spherical alkyl polyacrylate powder | 5 |
| Butyl ethyl propanediol | 0.5 |
| Purified water | Balance |
| Perfume | Q.S. |

Formulation Example 9

Gel

| | |
|---|---|
| Glycerin | 2 |
| 1,3-Butylene glycol | 4 |
| Potassium hydroxide | 0.1 |
| Fish collagen | 20 |
| Trisodium edetate | 0.05 |
| *Astraeus hygrometricus* liquid extract with 50% 1,3-butylene glycol (residual content when dried: 1%) | 1 |
| Carboxyvinyl polymer | 0.25 |
| Paraoxybenzoate | Q.S. |
| Purified water | Balance |

Formulation Example 10

Pack

| | |
|---|---|
| Dipropylene glycol | 5.0 |
| Polyoxyethylene (60 mol) hardened castor oil | 5.0 |
| *Onnia orientalis* extract with 50% ethanol | 0.01 |
| Olive oil | 5.0 |
| Tocopherol acetate | 0.2 |
| Ethylparaben | 0.2 |
| Perfume | 0.2 |
| Sodium hydrogensulfite | 0.03 |
| Polyvinyl alcohol (saponification degree: 90, polymerization degree: 2000) | 13.0 |
| Ethanol | 7.0 |
| Purified water | Balance |

Formulation Example 11

Emulsion Type Foundation

| | |
|---|---|
| Behenyl alcohol | 0.5 |
| Dipropylene glycol | 6 |
| Stearic acid | 1 |
| Glyceryl monostearate | 1 |
| Potassium hydroxide | 0.2 |
| Triethanolamine | 0.8 |
| DL-α-Tocopherol acetate | 0.1 |
| Paraoxybenzoate | Q.S. |
| Yellow iron oxide | 1 |
| α-Olefin oligomer | 3 |
| Dimethylpolysiloxane (6 mPa · s) | 2 |
| Dimethylpolysiloxane (100 mPa · s) | 5 |
| Batyl alcohol | 0.5 |
| Isostearic acid | 1 |
| Behenic acid | 0.5 |
| Cetyl 2-ethylhexanoate | 10 |
| Polyoxyethylene glyceryl monostearate | 1 |
| Titanium oxide | 3 |
| Titanated mica/alkyl polyacrylate composite powder | 0.5 |
| Surface treated titanium oxide (MT-062) | 10 |
| Alkyl polyacrylate coated titanated mica | 0.5 |
| Black iron oxide coated titanated mica | 0.5 |
| Silicic anhydride | 6 |
| 2-Ethylhexyl p-methoxycinnamate | 2 |
| Red iron oxide | Q.S. |
| Ultramarine | Q.S. |
| Black iron oxide | Q.S. |
| Legal color | Q.S. |
| Xanthan gum | 0.1 |
| Bentonite | 1 |
| Sodium carboxylmethyl cellulose | 0.1 |
| *Pleurotus abalonus* extract with ethanol | 0.1 |
| Purified water | Balance |
| Perfume | Q.S. |

Formulation Example 12

Solid Foundation

| | |
|---|---|
| Talc | 43.1 |
| Kaolin | 15.0 |
| Sericite | 10.0 |
| Zinc oxide | 7.0 |
| Titanium dioxide | 3.8 |

-continued

| | |
|---|---|
| Yellow iron oxide | 2.9 |
| Black iron oxide | 0.2 |
| Squalane | 8.0 |
| Isostearic acid | 4.0 |
| POE sorbitan monooleate | 3.0 |
| Isocetyl octanoate | 2.0 |
| *Pholiota squarrosa* extract with ethanol | 0.5 |
| Antiseptic | Q.S. |
| Perfume | Q.S. |

Composite Example 13

Milky Lotion

| | |
|---|---|
| Dimethylpolysiloxane | 2 |
| Decamethylcyclopentasiloxane | 25 |
| Dodecamethylcyclohexasiloxane | 10 |
| Polyoxyethylene/methyl polysiloxane copolymer | 1.5 |
| Trimethylsiloxysilicate | 1 |
| 1,3-Butylene glycol | 5 |
| Squalane | 0.5 |
| Talc | 5 |
| Dipotassium glycyrrhizinate | 0.1 |
| *Pleurotus nebrodensis* extract with ethanol | 0.1 |
| Tocopherol acetate | 0.1 |
| Trisodium edetate | 0.05 |
| 4-t-Butyl-4'-methoxydibenzoylmethane | 1 |
| 2-Ethylhexyl p-methoxycinnamate | 5 |
| Glyceryl mono-2-ethylhexanoate di-p-methoxycinnamate | 1 |
| Silicone coated titanium oxide fine particle (40 nm) | 4 |
| Dimethyl distearyl ammonium hectorite | 0.5 |
| Spherical polyethylene powder | 3 |
| Phenoxy ethanol | Q.S. |
| Purified water | Balance |
| Perfume | Q.S. |

Formulation Example 14

Cream

| | |
|---|---|
| Liquid paraffin | 8 |
| Vaseline | 3 |
| Dimethylpolysiloxane | 2 |
| Stearyl alcohol | 3 |
| Behenyl alcohol | 2 |
| Glycerin | 5 |
| Dipropylene glycol | 4 |
| Trehalose | 1 |
| Pentaerythritol tetra-2-ethylhexanoate | 4 |
| Polyoxyethylene glyceryl monoisostearate | 2 |
| Polyoxyethylene glyceryl monostearate | 1 |
| Lipophilic glyceryl monostearate | 2 |
| Citric acid | 0.05 |
| Sodium citrate | 0.05 |
| Potassium hydroxide | 0.015 |
| Oil soluble licorice extract | 0.1 |
| Retinol palmitate (1,000,0000 units) | 0.25 |
| Tocopherol acetate | 0.1 |
| *Pleurotus nebrodensis* extract with 50% ethanol | 0.1 |
| Paraoxybenzoate | Q.S. |
| Phenoxy ethanol | Q.S. |
| Dibutylhydroxytoluene | Q.S. |
| Trisodium edetate | 0.05 |
| 4-t-Butyl-4'-methoxydibenzoylmethane | 0.01 |
| 2-Ethylhexyl p-methoxycinnamate | 0.1 |
| β-Carotene | 0.01 |

-continued

| | |
|---|---|
| Polyvinyl alcohol | 0.5 |
| Hydroxyethyl cellulose | 0.5 |
| Carboxyvinyl polymer | 0.05 |
| Purified water | Balance |
| Perfume | Q.S. |

Formulation Example 15

Emulsion-Type Foundation

| | |
|---|---|
| Behenyl alcohol | 0.5 |
| Dipropylene glycol | 6 |
| Stearic acid | 1 |
| Glycerin monostegrate | 1 |
| Potassium hydroxide | 0.2 |
| Triethanolamine | 0.8 |
| DL-α-Tocopherol acetate | 0.1 |
| Paraoxybenzoate | Q.S. |
| Yellow iron oxide | 1 |
| α-Olefin oligomer | 3 |
| Dimethylpolysiloxane (6 mPa · s) | 2 |
| Dimethylpolysiloxane (100 mPa · s) | 5 |
| Batyl alcohol | 0.5 |
| Isostearic acid | 1 |
| Behenic acid | 0.5 |
| Cetyl 2-ethylhexanoate | 10 |
| Polyoxyethylene glyceryl monostearate | 1 |
| Titanium oxide | 3 |
| Titanated mica/alkyl polyacrylate composite powder | 0.5 |
| Surface treated titanium oxide (MT-062) | 10 |
| Alkyl polyacrylate coated titanated mica | 0.5 |
| Black iron oxide coated titanated mica | 0.5 |
| Silicic anhydride | 6 |
| 2-Ethylhexyl p-methoxycinnamate | 2 |
| Red iron oxide | Q.S. |
| Ultramarine | Q.S. |
| Black iron oxide | Q.S. |
| Legal color | Q.S. |
| Xanthan gum | 0.1 |
| Bentonite | 1 |
| Sodium carboxylmethyl cellulose | 0.1 |
| *Pleurotus nebrodensis* extract with ethanol | 0.1 |
| Purified water | Balance |
| Perfume | Q.S. |

What is claimed is:

1. A method for suppressing melanin generation comprising topically applying to the skin of a subject in need thereof a preparation comprising an effective amount of an extract of *Pleurotus nebrodensis*.

2. The method of claim 1, wherein the preparation includes, as dry weight, from 0.001 weight percent to 20 weight percent of the extract of *Pleurotus nebrodensis*.

3. The method of claim 1, wherein the preparation includes, as dry weight, from 0.01 weight percent to 10 weight percent of the extract of *Pleurotus nebrodensis*.

4. The method of claim 1, wherein the preparation further includes an externally acceptable carrier and/or adjuvant.

5. The method of claim 1, wherein the preparation further includes a UV-absorbent.

6. The method of claim 1, wherein the preparation further includes titanium oxide.

7. The method of claim 1, wherein the preparation further includes zinc oxide.

8. The method of claim 1, wherein the preparation is in a form selected from ointments, creams, milky lotions, lotions, packs, bath preparations, and foundations.

9. The method of claim 1, wherein the extract of *Pleurotus nebrodensis* inhibits tyrosinase activity.

10. The method of claim 1, wherein the extract of *Pleurotus nebrodensis* acts as a skin-whitening agent.

* * * * *